United States Patent [19]

Munro et al.

[11] Patent Number: 4,833,384
[45] Date of Patent: May 23, 1989

[54] SYRINGE DRIVE ASSEMBLY

[75] Inventors: Donald F. Munro; Robert R. Burnside, both of Mountain View; Donald M. Besemer, Los Altos Hills, all of Calif.

[73] Assignee: Syntex (U.S.A.) Inc., Palo Alto, Calif.

[21] Appl. No.: 75,371

[22] Filed: Jul. 20, 1987

[51] Int. Cl.[4] ............................................. A61M 5/315
[52] U.S. Cl. .................................. 318/687; 318/626; 128/DIG. 1
[58] Field of Search .......................... 128/655, DIG. 1; 222/14; 73/864.16; 422/100; 318/626, 687

[56] References Cited

U.S. PATENT DOCUMENTS

| | | | |
|---|---|---|---|
| 3,623,474 | 11/1971 | Heilman et al. | 128/655 |
| 3,631,847 | 1/1972 | Hobbs | 128/655 |
| 3,701,345 | 10/1972 | Heilman et al. | 127/655 |
| 3,858,581 | 1/1975 | Kamen | 128/DIG. 1 X |
| 4,006,736 | 2/1977 | Kranys et al. | 128/655 |
| 4,101,283 | 7/1978 | Sundstrom | 73/864.16 X |
| 4,108,177 | 8/1978 | Pistor | 128/DIG. 1 X |

Primary Examiner—Bentsu Ro
Attorney, Agent, or Firm—John A. Dhuey

[57] ABSTRACT

An assembly is described for accurately and precisely controlling the position of a plunger in a syringe to deliver precise fluid volumes. The assembly includes a motor coupled to a lead screw that drives a bearing block along a linear guide rod to move the plunger of the syringe in a linear fashion. The position of the plunger is accurately controlled by attaching a digital encoder to the rotating motor shaft. The encoder and associated electronics output to a controlling processor that generates a series of regular pulses, typically 300 to 500 responsive to each motor revolution. Utilizing appropriate gear ratios of the motor and the lead screw, the number of pulses per full syringe stroke in typical applications can be on the order of one hundred thousand. The final position and the motion of the plunger (velocity and acceleration) can be controlled to within a few encoder pulses, thus precisely controlling the rate of delivery of the fluid and the volume of the fluid actually delivered by the syringe. A closed positive feedback system is utilized to detect positional errors and obtain improved precision and accuracy.

4 Claims, 2 Drawing Sheets

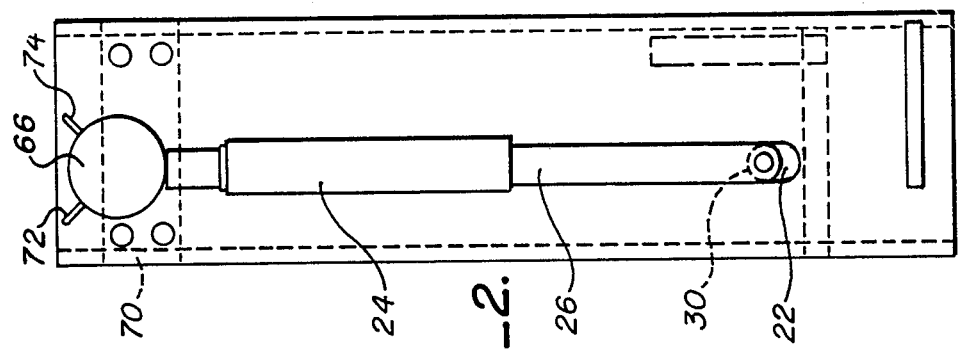
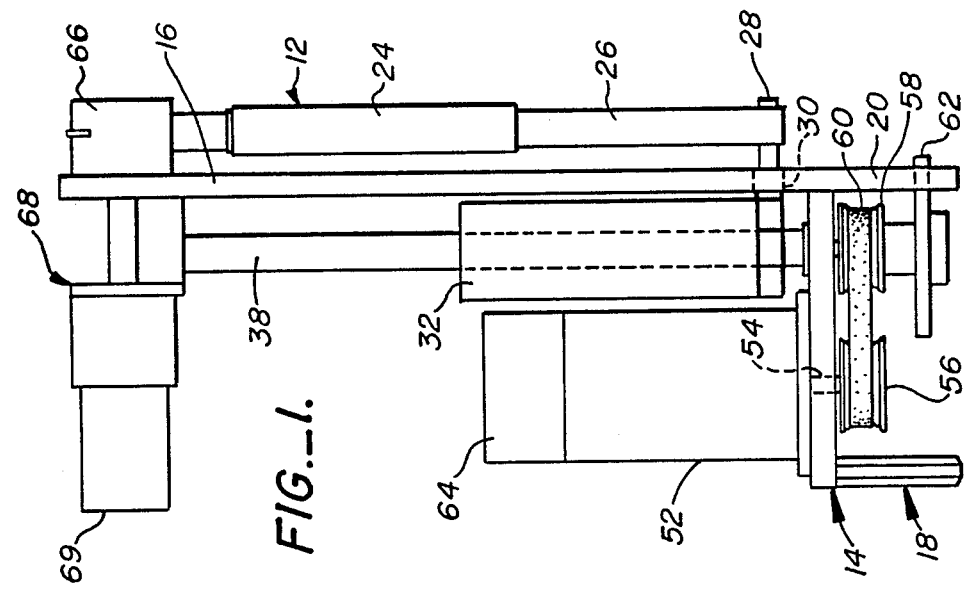
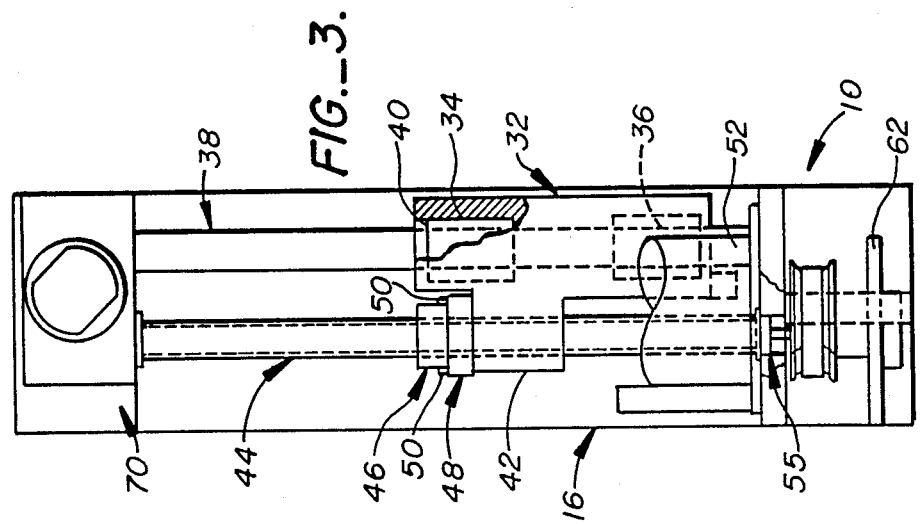

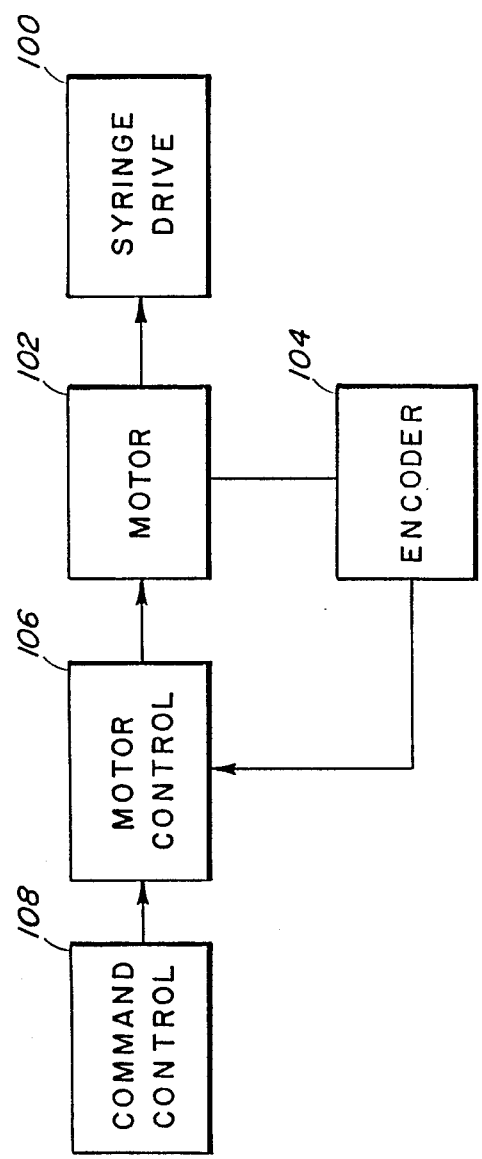
FIG._4.

SYRINGE DRIVE ASSEMBLY

BACKGROUND OF THE INVENTION

1. Field

The invention relates to an assembly for controlling fluid delivery via a syringe. In particular, the invention relates to a drive system coupled to the plunger of a syringe which is monitored and contorlled by an optical/electronic feedback system for precisely determining and controlling the position and motion (velocity and acceleration) of the plunger.

2. State of the Art

Present commercial clinical laboratory applications of syringe delivery systems typically include a stepper motor attached to a drive mechanism which is coupled to the plunger of a syringe. A typical example of such systems are digitial pumps such as the Cavro Modular Digital Pump, Model SB, manufactured and sold by Cavro Scientific Instruments, Inc., Sunnyvale California.

In conventional systems, the stepper motor usually has increments of resolution of not less than 1.8° per step (approximately 200 steps per revolution). Furthermore, no positional feedback loop is used to ensure accuracy and detect errors of motion. In practice it is not unusual, for example, that the control to the stepper motor will indicate that a determined number of programmed steps has been taken, but that the stepper motor in fact does not rotate the number of steps programmed. An error in the position of the plunger thus occurs and concomitantly an error in the amount and rate of delivery of fluid from the syringe will occur also. Accordingly, there is a need for an assembly which accurately and precisely controls and monitors the position and motion of the syringe plunger so that accurate amounts of fluid can be delivered. The present invention is considered to provide such assembly.

SUMMARY OF THE INVENTION

The present invention comprehends a syringe drive assembly comprising a syringe, including a syringe body and a plunger moveable within the body, drive means operably coupled to the plunger, primary control means directly coupled to the drive means, and sensing means associated with the drive means and the primary control means, the sensing means being operable to sense the temporal position of the drive means. The sensing means may sense the temporal position of the drive means indirectly from the temporal position of the primary control means. The sensing means includes feedback control means responsive to the sensed position of the primary control means of the drive means. In one aspect, the primary control means includes a motor having a rotatable shaft on which the sensing means is supported or fixed to generate a signal responsive to the temporal position of the shaft. The signal is utilized by the primary control means to further control the position and motion of the plunger. In a preferred embodiment, the sensing means includes an optical/electronic encoder coupled to a secondary controller for controlling input to the primary control means.

In another aspect, the syringe drive assembly comprises a base, a syringe having a body supported on the base and a plunger moveable within the body, drive means supported on the base and coupled to the plunger, motor means having a shaft coupled to the drive means, and sensing means associated with the shaft of the motor means for sensing the position of the shaft. The syringe drive assembly can include stabilizing means associated with the base and the drive means to facilitate linear movement of the plunger. The syringe drive assembly may include a support surface on the base which is parallel to the plunger, a slot in the parallel support surface and a bearing that rides within the slot as the plunger and the linear drive means moves in unison. Other aspects of the invention will be apparent from the figures and the detailed description of the invention which follows.

BRIEF DESCRIPTION OF THE DRAWINGS

FIG. 1 is a front elevational view of the syringe drive assembly of the present invention;

FIG. 2 is a side view of the invention illustrated in FIG. 1;

FIG. 3 is a view from the other side partially cut away, particularly illustrating the linear drive means and the linear guide means of the present invention; and FIG. 4 is a block diagram illustrating the control functions useful in the present invention.

DETAILED DESCRIPTION OF THE INVENTION

The invention deals with a syringe assembly for accurately and precisely controlling the position and motion of a plunger in a syringe body to deliver precise fluid volumes in a predetermined manner over time. The assembly includes drive means operably coupled to the plunger and a primary control means coupled to the drive means. The primary control means includes a motor, preferably a D-C motor, and a microprocessor control that controls both the position of the motor (i.e. the angular position of the motor shaft in its revolutionary movement) and the motion of the motor (i.e the angular acceleration and velocity of the motor shaft).

Since in a conventional syringe/plunger assembly the plunger is adapted to move linearly within the syringe body, the drive means utilzes elements that provide a linear drive system for the plunger. The plunger usually is required to move in one direction to draw fluid into the syringe body and in a second, opposite direction to deliver fluid from the syringe body. The drive means conveniently includes means for coupling the primary control means, in which the motor provides rotational movement, to the plunger while translating the rotational movement into linear movement. This is accomplished by directly coupling the output shaft of the motor to a lead screw. Means are provided on the lead screw to linearly traverse the lead screw when the lead screw rotates. Typically, a threaded nut is provided that is threaded on the lead screw and is attached by a suitable coupling means to the plunger. When the motor and lead screw rotate, the threaded nut traverses the lead screw and moves the plunger through the coupling mechanism.

Linear movement of the plunger if facilitated by the bearing block and support bearings that ride on a linear guide rod to promote movement parallel to that of the plunger. The threaded nut is allowed to "float" relative to the bearing block which functions as a portion of the coupling means and such a function dramatically reduces wear between the syringe plunger and the syringe body. Such a "float" typically is accomplished by attaching the nut to the bearing block by means of shoulder bolts or the like that permit relative movement between the bearing block and the threaded nut.

Additional stabilizing means can be provided between the aforementioned guide means and the plunger to further assure linear movement of the plunger. Such stabilizing means are conveniently provided by bearing means, which may include a slotted bearing track to retain a bearing means on a support coupled to the plunger between the guide means and the plunger.

The assembly also includes sensing means for detecting the temporal position of the plunger. Such means can detect both position and motion (i.e. velocity and acceleration) of the plunger. Most conveniently, sensing of the plunger parameters is accomplished indirectly by monitoring the position and motion of the primary control means while directly coupling the primary control means to the drive means. This is done by directly coupling the motor output shaft to the lead screw by a cogged belt, e.g. timing belt, or the like. By "directly coupling" is meant that there is substantially no lost motion between movement of the motor output shaft and the lead screw other than what might be experienced from usual belt or gear lash. The sensing means conveniently includes a signal generating means affixed to the motor output shaft that monitors the angular movement of the motor output shaft. Typically, one can use an optical/electronic encoder coupled to a microprocessor to sense the shaft position and instruct the primary control means to control the output shaft position. Feedback control means are provided within the primary control means for accurately and precisely controlling output shaft position and motion.

With particular reference to FIGS. 1, 2 and 3, the present invention includes a base 10 on which is supported a syringe 12. The base 10 includes a support plate 14, a face plate 16 and leg extensions 18 and 20. The leg extension 20 of face plate 16 can of course be intergally formed therewith. Extensions 18 and 20 provide space beneath support plate 14 for various hardware included in the present invention.

Syringe 12 includes a syringe body 24 in which is moveably located a syringe plunger 26. Syringe plunger 26 is connected to a support shaft 28 which has mounted thereon a stabilizing bearing 30, e.g. ball bearings or sliding bearings, which is adapted to ride in a bearing groove 22 in face plate 16. The end of shaft 28 remote from the syringe plunger 26 is attached to a bearing block 32, conventionally by simply being inserted into a hole near the bottom of the bearing block but other attachment means could be used as well. The bearing block 32 includes a first linear bearing 34 and a second linear bearing 36, e.g. each may be linear ball bearings, which are adapted to move along guide rod 38. An extension of bearing block 32 is provided by a sleeve 42 of which is attached a nut 46 having a flange 48. Nut 46 is threaded to mate with lead screw 44 and has a flange 48 formed thereon through which screws 50 attach nut 46 to sleeve 42. Screws 50 are shoulder screws which permit nut 46 to float relative to sleeve 42. In that manner, skewing of bearing block 32 by the turning motion of lead screw 44 and nut 46 is prevented. Accordingly, bearing block 32 rides easily along guide rod 38, preferably cylindrical, and facilitates linear movement of the plunger 26 in syringe body 24 greatly reducing the wear between the two. Extensive wear between plunger 26 and syringe body 24 will result in leakage that ultimately becomes unacceptable to the user. The present structure greatly minimizes wear, substantially increasing the cycle life of the syringe assembly.

Attached to one end of lead screw 44 is a pulley 58 which itself is operatively coupled via a belt 60 to another pulley 56 mounted on the end of the motor output shaft 54 of motor 52. Motor 52 is mounted on support plate 14. Belt 60 typically is a positive drive belt like a cogged or toothed belt, e.g. a timing belt or timing chain, which is adapted to mate with complimentary grooves in pulleys 56 and 58 to provide a direct coupling between the output shaft 54 of motor 52 and lead screw 44. Such direct coupling substantially prevents any slipping of belt 60 and reduces lost motion between pulley 56 and pulley 58. A thumb wheel 62 is provided at the end of lead screw 44 to provide for manual operation of the lead scew when necessary. The thumb wheel function allows the operator to manipulate the syringe while the power is off, for example to change seals between the plunger and the syringe body.

Directly coupled to the output shaft 54 is an encoder 64 which is adapted to interface with a control system, typically a microprocessor, to monitor the exact position of motor output shaft 54. A variety of encoder/control systems are available, for example the HCTL-1000 from Hewlett Packard, Palo Alto, California and the Model 4327 Servo Motor Controller of Technology 80 Inc., Minneapolis, Minnesota are useful.

The fluid delivery system additionally includes a valve 66, that may be two-way, having an inlet 72 and outlet 74, and a valve motor 68, typically a DC motor operated at less than 48 volts, on which is mounted a valve motor control 69. A support block 70 attached to face plate 16 is utilized to support the valve motor 68 and valve motor control 69. Valve motor control 69 interfaces with a microprocessor control system such that the position of valve 66 is appropriately controlled when fluid is being added to the syringe or dispensed therefrom.

The control mechanism is illustrated schematically in FIG. 4. As described and illustrated there, the syringe drive 100 is controlled by a motor means 102 which is coupled to an encoder 104. Encoder 104 transmits signals to motor control 106 which utilizes such signals for the primary control of motor means 102. In addition, a command control 108 inputs information to motor control 106 to provide the desired position and motion control of syringe 100. In actual practice, the command control 108 controls voltage to a DC motor 52 and tracks the position of encoder 64. Encoder 64 typically and illustratively is an optical system that may commercially obtained, including a wheel having a grating disposed thereon which is interposed between a light source, for example a light emitting diode and a sensor, typically a phototransistor. Since the wheel is connected directly to the motor shaft, and the motor shaft rotates, pulses are created between the source and the sensor which monitors acceleration, deceleration and total movement. Those signals are fed into motor control 106 which monitors the position and the motion (velocity and acceleration) of motor shaft 54. Since motor shaft 54 is directly coupled to lead screw 44, movement and position of motor shaft 54 directly relates to movement and position of lead screw 44. Additionally, since bearing block 32 is directly coupled to syringe plunger 26, accurate monitoring of the position and motion of syringe plunger 26 is effected. The difference between the desired position of the motor and the actual position of the motor as determined by the encoder is the position error. By utilizing an encoder wheel with 500 slots and a sensor source combination with two light emitting diodes 90° out of phase, up to 2,000 positions of the motor shaft can be monitored. Typically, the lead screw will have 16/18 threads per inch. although coarser threading may be used but then generally with a finer grating system on the encoder wheel. Syringe volumes may range from 10 microliters to hundreds of milliliters (although larger volumes will generally require the ganging of syringes of lesser volume to maintain delivery accuracy), but most typically not more than 5 to 10 milliliters for clinical laboratory applications. The number of pulses available in a syringe stroke of approximately 6 centimeters can approximate over 100,000. Such fine tuning provides for very accurate control of syringe plunger 26.

In operation, to add fluid to the syringe, command control 108 is set by an operator to drive ouput shaft 54 of motor 52 to a determined position. At the same time, command control 108 will instruct valve motor control 69 to open inlet 72 to allow liquid to be drawn into syringe body 24 from a source (not shown). Upon actuation by the operator, motor output shaft 54 will be actuated to move a predetermined position in accordance with a programmed motion. As output shaft 54 rotates, motion is transferred to lead screw 44 via pulleys 56 and 58 and belt 60. As lead screw 44 rotates, it will drive nut 46, which, because of its attachment to sleeve 42, drives bearing block 32 along guide rod 38. As the bearing block 32 moves downwardly, it pulls plunger 26 through the direct coupling with support shaft 28. Bearing 30 rides in bearing slot 22 as plunger 26 descends.

As output shaft 54 rotates, encoder 64 sends signals, i.e. a pulse train, back to motor control 106. The controller compares the decoded motor position with the commanded position and determines the position error. The controller utilizes the position error (and usually a derivative signal) to form a motor command which adjusts the motion of motor 52 based on that feedback signal. When the plunger 26 has reached the end of its travel, motor control 106 stops motor 52 since there is no longer any difference between the actual position of the motor and the commanded position of the motor. The dispensing of the liquid is controlled by the command control 108 in substantially the manner described previously. Valve 66 switches to outlet 74 and output shaft 54 is rotated in the opposite direction to move plunger 26 upwardly. Motion and control of the upward movement of the plunger 26 is effected and monitored as described above.

For illustration purposes encoder 64 has been placed on the end of motor shaft 54. The encoder 64 could also be placed on the end of lead screw 44. Various other mechanisms of direct coupling of the motor 52 to lead screw 54, for example direct gearing and the like, can be provided .

While the foregoing invention has been described with reference to the drawings, and the presently preferred embodiments, there are intended to be illustrative and not intended to limit the scope of the invention claimed. Various modifications or changes to the methods and apparatus described herein will be apparent to those skilled in the art and are intended to be included and encompassed by the claims appended hereto.

What is claimed is:

1. A syringe drive assembly comprising:
   a base having a linear bearing surface thereon;
   a syringe having a body supported on said base adjacent and substantially parallel to said bearing surface and a plunger moveable within said body;
   a linear drive screw supported on said base, substantially parallel to said body and coupled to said plunger by a support shaft, said support shaft having a bearing mounted thereon and adapted to move on said bearing surface to stabilize said plunger during linear movement thereof;
   motor means having an output shaft coupled to said linear drive screw; and
   sensing means associated with said output shaft of said motor means for sensing the position of said support shaft.

2. The assembly of claim 1 wherein said bearing surface is formed by a linear slot parallel to said plunger and said bearing is moveable within said slot.

3. The assembly of claim 1 including guide means mounted on said base wherein said linear drive screw is coupled to said guide means by coupling means threaded on said screw and movably attached to said guide means to permit relative movement therebetween.

4. The assembly of claim 3 wherein said coupling means includes a nut threaded on said drive screw, a guide rod parallel to said screw and a bearing block adapted to move linearly along said guide rod in response to motion of said drive screw, said nut being fixed to said bearing block in a manner allowing limited movement between said nut and said bearing block.

* * * * *